United States Patent [19]
Mendes et al.

[11] Patent Number: 5,549,660
[45] Date of Patent: Aug. 27, 1996

[54] METHOD OF TREATING ACNE

[75] Inventors: Emanuel Mendes, Petach Tikva; Gideon Iron; Avikam Harel, both of Tel Aviv, Israel

[73] Assignee: Amron, Ltd., Tel Aviv, Israel

[21] Appl. No.: 973,374

[22] Filed: Nov. 12, 1992

Related U.S. Application Data

[63] Continuation-in-part of Ser. No. 615,050, Nov. 15, 1990, Pat. No. 5,259,380.

[30] Foreign Application Priority Data

Jun. 5, 1992 [IL] Israel ......................................... 102125

[51] Int. Cl.$^6$ ......................................................... A61N 5/00
[52] U.S. Cl. ........................... 607/088; 606/3; 606/9
[58] Field of Search .............................. 128/633, 664–6; 606/3, 13, 2, 9, 12; 607/88–90, 94–5

[56] References Cited

U.S. PATENT DOCUMENTS 4,930,504   6/1990   Diamantopoulos et al. ........... 606/3 X
5,259,380  11/1993   Mendes et al. ........................ 606/3 X

FOREIGN PATENT DOCUMENTS 2212010A  of 1989  United Kingdom.

*Primary Examiner*—Angela D. Sykes
*Attorney, Agent, or Firm*—Natter & Natter

[57] ABSTRACT

A method of treating acne by illumination comprising the steps of utilizing at least one light emitting diode (LED) by driving each of the at least one LEDs in substantially continuous wave (CW) mode of operation to generate CW light radiation in a narrow bandwidth centered at a wavelength suitable for acne relief, concentrating and projecting the CW light radiation onto an acne-affected dermal zone for biostimulative treatment thereof and maintaining the light radiation for a prescribed treatment duration, wherein each of the at least one LEDs emits light of substantially the same wavelength and wherein the acne affected dermal zone is not simultaneously illuminated by stimulating radiation of another wavelength.

10 Claims, 2 Drawing Sheets

5,549,660

METHOD OF TREATING ACNE

RELATED APPLICATIONS

This application is a continuation-in-part of application Ser. No. 615,050, filed Nov. 15, 1990 now U.S. Pat. No. 5,259,380.

FIELD OF THE INVENTION

The present invention relates to apparatus and a method for light therapy.

BACKGROUND OF THE INVENTION

Acne vulgaris is a disfiguring ailment of the skin. It is typically very troublesome to the sufferer.

Light therapy is known for treating a variety of patient complaints and ailments. A state of the art device suitable for administering light therapy is disclosed in U.S. Pat. 4,930,504 to Diamantopoulos et al. Diamantopoulos et al hypothesize that the disclosed device may be used, "for example, to treat inflammations, wounds burns, chronic ulcerations including diabetic ulcers, deficient circulation, pain, nerve degeneration, eczema, shingles, infection, scars, acne, bone fractures, muscle and ligament injuries, arthritis, osteoarthritis, rheumatiodal arthritis, skin grafts, gingival irritation, oral ulcers, dental pain and swelling, cellulitis, stretch marks, skin tone, alopecia areata, trigeminal neuralgia, herpes, zosten, sciatica, cervical erosions and other conditions."

Diamantopoulos et al teach the use of an array of substantially monochromatic radiation sources of a plurality of wavelengths, preferably of at least three different wavelengths. The sources radiate in accordance with a high duty-cycle pulsed rate, and are arranged within the array such that radiation of at least two different wavelengths passes directly or indirectly through a single point located within the treated tissue.

Use of LEDs in administering light therapy for the treatment of certain ailments and complaints is disclosed in Applicant's published UK Application GB 2212010A.

SUMMARY OF THE INVENTION

The present invention seeks to provide an apparatus and a method for therapeutic illumination which are particularly suited for treatment of acne.

There is thus provided in accordance with a preferred embodiment of the present invention a method of relieving acne by illumination including the steps of utilizing at least one light emitting diode (LED) by driving each of the at least one diodes in a substantially continuous wave (CW) mode to generate light radiation in a narrow bandwidth centered at a wavelength suitable for acne relief, concentrating the light of the at least one diodes and projecting the light to an acne-affected dermal zone for biostimulative treatment thereof and maintaining the light radiation for a prescribed treatment duration.

In accordance with a preferred embodiment of the present invention there is also provided a method of relieving acne by illumination including the steps of utilizing at least one light emitting diode (LED) emitting non-coherent substantially single frequency light in a narrow bandwidth centered at a wavelength suitable for acne relief, concentrating the light of the at least one diodes and projecting the light to an acne-affected zone for biostimulative treatment thereof and maintaining the light radiation for a prescribed treatment duration, wherein the light emitted by each of the plurality of diodes has substantially the same wavelength and wherein the acne affected dermal zone is not simultaneously illuminated by stimulating radiation of another wavelength.

Further in accordance with a preferred embodiment of the present invention, the plurality of LEDs is arranged along a plane and preferably includes one or more circular or linear arrays of LEDs.

Still further in accordance with a preferred embodiment of the present invention, the narrow bandwidth comprises a red light bandwidth having a wavelength of approximately 660 nm.

Still further in accordance with a preferred embodiment of the present invention, each of the LEDs emits a cone of light, and the LEDs are configured and arranged such that the plurality of cones of light emitted by the LEDs intersects over the zone.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
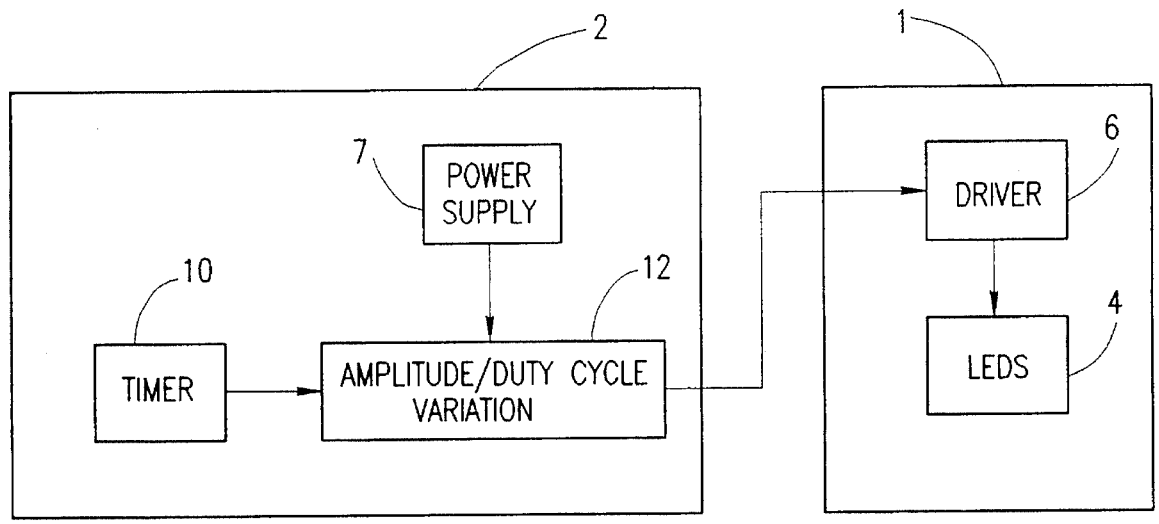
FIG. 1 is a simplified block diagram functionally showing apparatus constructed and operative in accordance with a preferred embodiment of the present invention.

Referring to FIG. 1, there is shown a compact light source 1 and an associated control unit 2 which preferably has a CW (continuous wave) mode of operation. The light source 1 comprises a plurality of LEDs 4 which receive power via a driver circuit 6. Preferably, each of the LEDs 4 emits light of substantially the same frequency. The control unit 2 contains a power supply 7 and a timer 10 which can be constituted by a standard clock circuit provided with "set time" switches, and whose function is to disable the control circuit 2 after a preset time has elapsed.

An amplitude and/or duty cycle variation circuit 12 provides a d.c. signal with a variable amplitude and/or duty cycle which is fed to the driver 6 of the light source 1. Thus, the light source 1 emits light continuously with a magnitude and/or duty cycle determined by amplitude/duty cycle variation circuit 12.

In a preferred embodiment of the invention, LEDs 4 are driven by driver 6 in accordance with CW mode of operation controlled by control unit 2. Experimental results show that a pure CW mode of operation is more effective than either a PW (pulsed wave) mode or any combination of the two modes.

Figure 2:
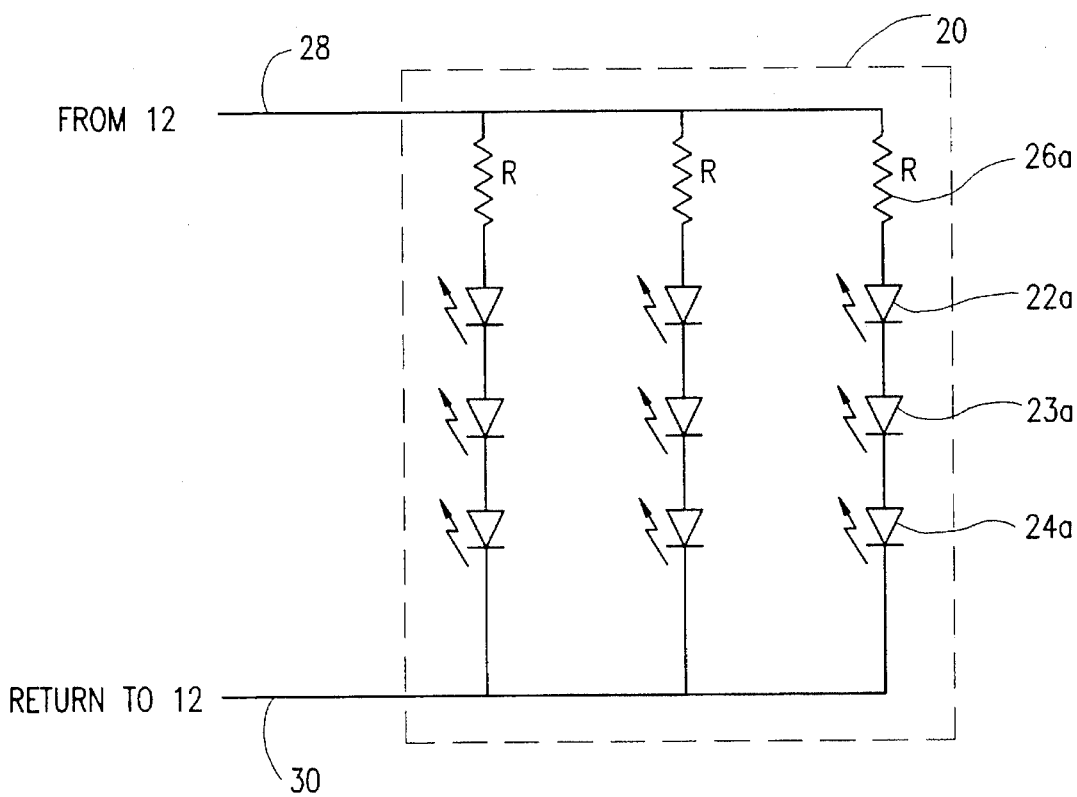
FIG. 2 shows the LEDs of FIG. 1 in greater detail.

FIG. 2 shows a preferred embodiment of LEDs in detail. The LEDs 4 are arranged in the form of an LED matrix 20 comprising a plurality of parallel branches each of which contains a predetermined number of LEDs connected in series. Thus, in FIG. 2, three LEDs 22a, 23a and 24a are connected in series and constitute one parallel branch of the diode matrix 20. The current flowing through this branch is limited by means of a series resistor 26a, and the resulting branch is connected between a high voltage d.c. rail 28 and a low voltage d.c. rail 3 . Thus, one terminal of the series connected current-limiting resistor is connected to the high voltage rail whilst the cathode of LED 24a is connected to the low voltage rail 3. The connection of all other branches of the LED matrix 25 is identical.

According to an alternative embodiment, series resistor 26a and power supply 7 may be replaced by a current source.

Figure 3:
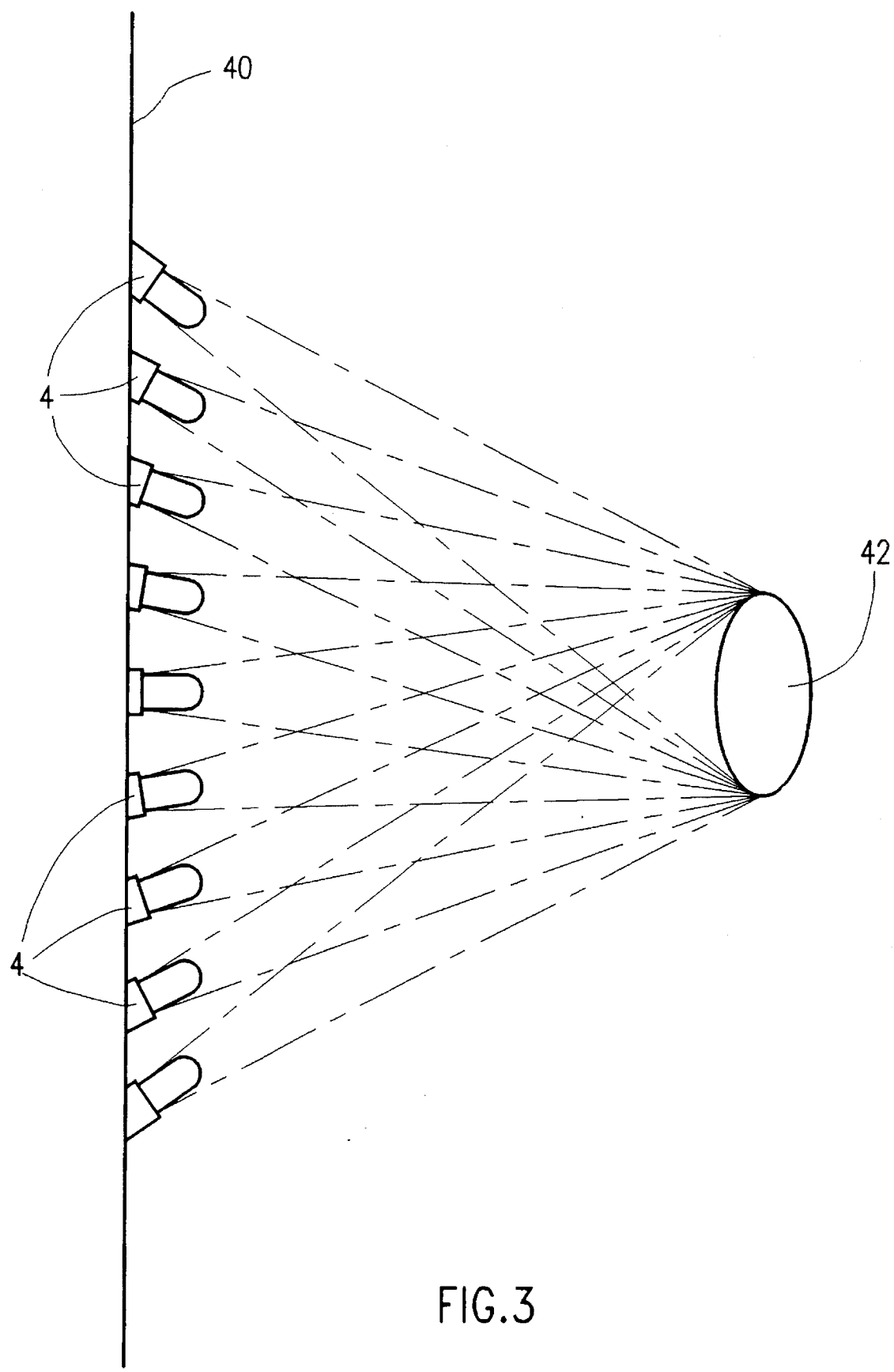
FIG. 3 shows a preferred arrangement for the physical connections of the LEDs shown schematically in FIG. 2.

FIG. 3 shows a preferred arrangement for the physical connections of the LEDs shown schematically in FIG. 2. The LEDs are preferably disposed on a planar surface 40, and are arranged along and angled with respect to the planar surface, such that their light outputs illuminate a defined area 42 such as an acne-afflicted portion of skin. In a preferred embodiment, the area which the LEDs illuminate is substantially circular with a diameter of approximately 1.2 cm. The LEDs may be arranged in any suitable manner on planar surface 40, such as in one, two or more concentric circles, or such as in one or more linear arrays. It will be understood that the greater the number of LEDs connected within the LED matrix 20 of FIG. 2, the greater will be the intensity of the light output by the light source 1 (FIG. 1).

It will be appreciated that each of the LEDs emits a cone of light, and the LEDs are configured and arranged such that the plurality of cones of light emitted by the plurality of LEDs intersects over the area 42, thereby concentrating their illumination on area 42.

The operation of the system is as follows. The amplitude and/or duty cycle variation circuit 12 operates so as to provide d.c. voltage with variable amplitude and/or duty cycle between the high voltage supply rail 28 and the ground terminal 30. Thus, by varying the setting of the amplitude/duty cycle variation circuit 12, the overall current flowing through the LED matrix 20 may be varied, and, therefore, the light intensity of the light source 1. As mentioned above, it is preferred that variation circuit 12 is set to a substantially continuous-wave mode of operation.

A preferred power level is approximately 10–30 mW/cm$^2$, such as 20 mW/cm$^2$.

Thus, the invention affords low cost apparatus for treating acne by producing a non-coherent source of illumination, preferably in CW mode, which is focussed over a small area. The exact wavelength of the illumination is confined within a relatively narrow bandwidth (+/–25 nm) and its central value may be predetermined by suitable selection of the LEDs in the LED matrix 20. Experimental evidence indicates that red light, such as 660 nm light, is particularly suitable for the treatment of acne. The average intensity of the emitted illumination may easily be varied by the operator, and the therapy time may be preset by means of the integral timer circuit which is preferably provided.

It will be appreciated that the particular features of the methods and apparatus shown and described herein may be employed separately or in combination in any suitable manner so as to enhance efficacy of treatment.

Variations on the apparatus shown and described herein are disclosed in Published UK application GB 2212010A. However, it is believed that the embodiment described hereinabove with reference to FIGS. 1–3 is a preferred embodiment for treatment of acne. Supporting experimental results are now described.

The first experiment relates to the search for an efficient wavelength to be used in the method of treating acne described hereinabove. In a double blind study, three groups of acne-afflicted patients, each group consisting of 10 patients, were compared. The first group was a control group which was treated by placebo only. The second group was exposed to CW IR radiation combined with some additional red radiation, generated by an array of LEDs. The third group was exposed to CW red-wavelength illumination (660 nm) only, generated by an array of LEDs. Statistical analysis of the results indicated that the treatment was not significantly more effective than the placebo treatment. However, the red-wavelength treatment was found to be effective at a statistically significant level.

Although this first experiment had been performed using red light radiation of 660 nm, it should be appreciated that other wavelengths which can be used may yield comperative results.

The second experiment compared between the CW mode of operation, which is utilized in a preferred embodiment of the present invention, and a combination mode which includes both a CW and a PW (pulsed wave) modes of operation, wherein both modes use arrays of LEDs as light sources. The CW mode proved to be effectively suitable for acne relief.

The results of these and other experiments indicate that most effective acne treatment results are achieved when using light in the red bandwidth illuminated in a CW mode of operation.

It will be appreciated by persons skilled in the art that the present invention is not limited to what has been particularly shown and described hereinabove. Rather, the scope of the present invention is defined only by the claims that follow:

We claim:

1. A method of treating acne with red light radiation, the method comprising the steps of:

(a) providing a plurality of light emitting diodes which generate non-coherent radiation in a narrow bandwidth centered at a wavelength of approximately 660 nm, (b) driving the diodes exclusively in a continuous wave mode to generate the non-coherent radiation, (c) concentrating and projecting the non-coherent radiation on a dermal area afflicted with acne without simultaneously illuminating the area with non-coherent light emitting diode radiation centered about a different wavelength and (d) maintaining the concentrating and projecting step (c) for a prescribed treatment duration.

2. A method of treating acne with red light radiation in accordance with claim 1 wherein the radiation is concentrated and projected on the acne afflicted area with an illumination power in the range of between 10 and 30 mw/cm$^2$.

3. A method of treating acne with red light radiation in accordance with claim 1 wherein the radiation is concentrated and projected on the acne afflicted area in a substantially circular pattern.

4. A method of treating acne with red light radiation in accordance with claim 3 wherein the substantially circular pattern has a diameter in the order 1 cm.

5. A method of treating acne with red light radiation in accordance with claim 4 wherein the diameter is in the order of 1.2 cm.

6. A method of treating acne with red light radiation in accordance with claim 3 wherein the step of concentrating and projecting the non-coherent radiation includes the steps of projecting a cone of light from each light emitting diode of the plurality and of directing the cones of light to intersect in the circular pattern.

7. A method of treating acne with red light radiation in accordance with claim 1 wherein the step of driving the diodes exclusively in a continuous wave mode to generate non-coherent radiation includes the step of controlling the intensity of the non-coherent radiation by controlling the amplitude and duty cycle at which the light emitting diodes are being driven.

8. A method of treating acne with red light radiation in accordance with claim 1 wherein the step of concentrating and projecting the non-coherent radiation includes the step of mounting the plurality of diodes in a planar array.

9. A method of treating acne with red light radiation in accordance with claim 8 wherein the step of mounting includes mounting the plurality of diodes in at least one circular array.

10. A method of treating acne with red light radiation in accordance with claim 8 wherein the step of mounting includes mounting the plurality of diodes in at least one linear array.

* * * * *